(12) United States Patent
Grinvald et al.

(10) Patent No.: US 8,403,862 B2
(45) Date of Patent: Mar. 26, 2013

(54) TIME-BASED IMAGING

(75) Inventors: Amiram Grinvald, Rehovot (IL); Darin Nelson, Misgav Dov (IL); Harel Primack, Rishon le Zion (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 806 days.

(21) Appl. No.: 12/340,889

(22) Filed: Dec. 22, 2008

(65) Prior Publication Data
US 2009/0163827 A1  Jun. 25, 2009

Related U.S. Application Data

(60) Provisional application No. 61/009,055, filed on Dec. 20, 2007.

(51) Int. Cl.
*A61B 3/00* (2006.01)
*A61B 18/00* (2006.01)
*A61B 18/18* (2006.01)
*A61B 3/10* (2006.01)

(52) U.S. Cl. ........ 600/558; 351/200; 351/206; 351/221; 435/288.7; 600/310; 600/317; 600/318; 600/323; 600/324; 600/476; 600/477; 600/544

(58) Field of Classification Search .................. 351/200, 351/206, 221; 435/288.7; 600/310, 317, 600/318, 323, 324, 476, 477, 544, 558
See application file for complete search history.

(56) References Cited

U.S. PATENT DOCUMENTS

| | | | |
|---|---|---|---|
| 4,336,459 A * | 6/1982 | Fay | .............. 250/459.1 |
| 4,621,643 A | 11/1986 | New, Jr. et al. | |
| 4,718,417 A | 1/1988 | Kittrell et al. | |
| 4,998,533 A | 3/1991 | Winkelman | |
| 5,217,456 A | 6/1993 | Narciso, Jr. | |
| 5,240,006 A | 8/1993 | Fujii et al. | |
| 5,279,298 A | 1/1994 | Flower | |
| 5,297,554 A | 3/1994 | Glynn et al. | |

(Continued)

FOREIGN PATENT DOCUMENTS

| | | |
|---|---|---|
| CN | 2151483 | 12/1993 |
| EP | 1302158 A2 | 4/2003 |

(Continued)

OTHER PUBLICATIONS

Sato Y et al., "Automatic extraction and measurement of leukocyte motion in microvessels using spatiotemporal image analysis", IEEE Trans. on Biomedical Engineering, IEEE Inc. New York, US, vol. 44, No. 4, Apr. 1, 1997.

(Continued)

*Primary Examiner* — Sean Dougherty
(74) *Attorney, Agent, or Firm* — Fish & Richardson P.C.

(57) ABSTRACT

A method includes directing toward a portion of a subject's body a first pulse of electromagnetic energy. While the portion is in a functional state due to the first pulse, a second pulse is directed toward the portion. At a second-pulse time, reflected energy due to the second pulse is detected. While the portion is in a functional state due to the first and second pulses, a third pulse is directed toward the portion. At a third-pulse time, energy of the third pulse, reflected from the portion, is detected. In response to detecting the pulses at the second-pulse time and the third-pulse time, a characteristic of the portion is quantified resulting from (a) the functional state due to the first pulse and (b) the functional state due to the first and second pulses. A clinical state of the subject is identified. Other embodiments are described.

43 Claims, 5 Drawing Sheets

U.S. PATENT DOCUMENTS

| | | | |
|---|---|---|---|
| 5,348,003 A | 9/1994 | Caro | |
| 5,400,091 A | 3/1995 | Okazaki | |
| 5,463,426 A | 10/1995 | Grinvald et al. | |
| 5,515,847 A | 5/1996 | Braig et al. | |
| 5,572,996 A | 11/1996 | Doiron et al. | |
| 5,598,842 A | 2/1997 | Ishihara et al. | |
| 5,666,956 A | 9/1997 | Buchert | |
| 5,706,821 A | 1/1998 | Matcher et al. | |
| 5,720,291 A | 2/1998 | Schwartz | |
| 5,722,398 A | 3/1998 | Ishihara et al. | |
| 5,741,213 A | 4/1998 | Kouchi et al. | |
| 5,769,076 A | 6/1998 | Maekawa et al. | |
| 5,784,162 A | 7/1998 | Cabib et al. | |
| 5,787,185 A | 7/1998 | Clayden | |
| 5,791,345 A | 8/1998 | Ishihara et al. | |
| 5,811,814 A | 9/1998 | Leone et al. | |
| 5,931,779 A | 8/1999 | Arakaki et al. | |
| 5,934,278 A | 8/1999 | Ishihara et al. | |
| 5,974,338 A | 10/1999 | Asano et al. | |
| 5,983,120 A | 11/1999 | Groner et al. | |
| 6,061,583 A | 5/2000 | Ishihara et al. | |
| 6,081,612 A | 6/2000 | Gotkowicz-Krusin et al. | |
| 6,088,087 A | 7/2000 | Graves et al. | |
| 6,104,939 A | 8/2000 | Groner et al. | |
| 6,116,736 A * | 9/2000 | Stark et al. | 351/206 |
| 6,208,749 B1 | 3/2001 | Gutkowicz-Krusin et al. | |
| 6,244,712 B1 | 6/2001 | Smith et al. | |
| 6,350,431 B1 | 2/2002 | Snow et al. | |
| 6,351,663 B1 | 2/2002 | Flower et al. | |
| 6,362,175 B1 | 3/2002 | Vinogradov et al. | |
| 6,478,424 B1 | 11/2002 | Grinvald et al. | |
| 6,512,936 B1 | 1/2003 | Monfre et al. | |
| 6,512,937 B2 | 1/2003 | Blank et al. | |
| 6,567,678 B1 | 5/2003 | Oosta et al. | |
| 6,571,118 B1 | 5/2003 | Utzinger et al. | |
| 6,587,701 B1 | 7/2003 | Stranc et al. | |
| 6,588,901 B1 | 7/2003 | Grinvald et al. | |
| 6,721,582 B2 | 4/2004 | Trepagnier et al. | |
| 6,782,289 B1 | 8/2004 | Strauss | |
| 6,820,979 B1 * | 11/2004 | Stark et al. | 351/206 |
| 6,826,424 B1 | 11/2004 | Zeng et al. | |
| 6,840,622 B2 * | 1/2005 | Kutschbach et al. | 351/200 |
| 6,844,195 B2 | 1/2005 | Craine | |
| 6,859,658 B1 | 2/2005 | Krug | |
| 6,869,430 B2 | 3/2005 | Balbierz et al. | |
| 6,889,075 B2 | 5/2005 | Marchitto et al. | |
| 6,898,451 B2 | 5/2005 | Wuori | |
| 6,898,458 B2 | 5/2005 | Zeng et al. | |
| 6,902,935 B2 | 6/2005 | Kaufman et al. | |
| 6,917,038 B2 | 7/2005 | Zheng et al. | |
| 6,957,094 B2 * | 10/2005 | Chance et al. | 600/310 |
| 7,025,765 B2 | 4/2006 | Balbierz et al. | |
| 7,054,674 B2 | 5/2006 | Cane et al. | |
| 7,115,841 B2 | 10/2006 | Zeng et al. | |
| 7,130,672 B2 * | 10/2006 | Pewzner et al. | 600/324 |
| 7,190,452 B2 | 3/2007 | Zeng et al. | |
| 7,217,266 B2 | 5/2007 | Anderson et al. | |
| 7,225,005 B2 | 5/2007 | Kaufman et al. | |
| 7,253,894 B2 | 8/2007 | Zeng et al. | |
| 7,280,678 B2 * | 10/2007 | Haven et al. | 382/117 |
| 7,334,895 B2 * | 2/2008 | Kandel et al. | 351/221 |
| 7,418,115 B2 * | 8/2008 | Northcott et al. | 382/117 |
| 7,488,073 B2 * | 2/2009 | Kandel et al. | 351/221 |
| 7,490,939 B2 * | 2/2009 | Hirohara et al. | 351/205 |
| 7,836,894 B2 * | 11/2010 | Brinkmann et al. | 128/898 |
| 2001/0031920 A1 | 10/2001 | Kaufman et al. | |
| 2001/0056237 A1 | 12/2001 | Cane et al. | |
| 2002/0007122 A1 | 1/2002 | Kaufman et al. | |
| 2002/0007123 A1 | 1/2002 | Balas | |
| 2002/0016533 A1 | 2/2002 | Marchitto et al. | |
| 2002/0016534 A1 | 2/2002 | Trepagnier et al. | |
| 2002/0024633 A1 * | 2/2002 | Kim et al. | 351/206 |
| 2002/0026127 A1 | 2/2002 | Balbierz et al. | |
| 2002/0026188 A1 | 2/2002 | Balbierz et al. | |
| 2002/0035358 A1 * | 3/2002 | Wang | 606/5 |
| 2002/0076820 A1 | 6/2002 | Craine | |
| 2002/0103439 A1 | 8/2002 | Zeng et al. | |
| 2002/0111545 A1 | 8/2002 | Lindberg et al. | |
| 2002/0127735 A1 | 9/2002 | Kaufman et al. | |
| 2002/0197728 A1 | 12/2002 | Kaufman et al. | |
| 2003/0032064 A1 | 2/2003 | Soller et al. | |
| 2003/0036693 A1 | 2/2003 | Avinash et al. | |
| 2003/0036751 A1 | 2/2003 | Anderson et al. | |
| 2003/0050541 A1 | 3/2003 | Wuori | |
| 2003/0074028 A1 | 4/2003 | Breithardt et al. | |
| 2003/0114762 A1 | 6/2003 | Balas et al. | |
| 2003/0146385 A1 | 8/2003 | Zheng et al. | |
| 2003/0163049 A1 | 8/2003 | Balas | |
| 2003/0207250 A1 | 11/2003 | Kaufman et al. | |
| 2004/0015211 A1 | 1/2004 | Nurmikko et al. | |
| 2004/0044287 A1 | 3/2004 | Lin et al. | |
| 2004/0054270 A1 * | 3/2004 | Pewzner et al. | 600/341 |
| 2004/0105075 A1 * | 6/2004 | Kandel et al. | 351/221 |
| 2004/0116814 A1 | 6/2004 | Stranc et al. | |
| 2004/0170304 A1 * | 9/2004 | Haven et al. | 382/115 |
| 2004/0189940 A1 * | 9/2004 | Kutschbach et al. | 351/212 |
| 2005/0046793 A1 * | 3/2005 | Hirohara et al. | 351/200 |
| 2005/0054936 A1 | 3/2005 | Balas | |
| 2005/0064602 A1 | 3/2005 | Kaufman et al. | |
| 2005/0090751 A1 | 4/2005 | Balas | |
| 2005/0131284 A1 | 6/2005 | Grinvald et al. | |
| 2005/0143662 A1 | 6/2005 | Marchitto et al. | |
| 2005/0167621 A1 | 8/2005 | Zeng et al. | |
| 2005/0177140 A1 * | 8/2005 | Jay | 606/9 |
| 2005/0192493 A1 | 9/2005 | Wuori | |
| 2005/0203421 A1 | 9/2005 | Zeng et al. | |
| 2005/0203423 A1 | 9/2005 | Zeng et al. | |
| 2005/0234315 A1 * | 10/2005 | Mayevsky et al. | 600/310 |
| 2005/0251049 A1 | 11/2005 | Cane et al. | |
| 2006/0082725 A1 * | 4/2006 | Yamaguchi et al. | 351/200 |
| 2006/0122524 A1 | 6/2006 | Kawada et al. | |
| 2006/0131284 A1 | 6/2006 | Sun et al. | |
| 2006/0141633 A1 | 6/2006 | Balas | |
| 2006/0147897 A1 | 7/2006 | Grinvald et al. | |
| 2006/0184037 A1 * | 8/2006 | Ince et al. | 600/476 |
| 2006/0195022 A1 | 8/2006 | Trepagnier et al. | |
| 2006/0241577 A1 | 10/2006 | Balbierz et al. | |
| 2007/0030447 A1 * | 2/2007 | Yamaguchi et al. | 351/206 |
| 2007/0043341 A1 | 2/2007 | Anderson et al. | |
| 2007/0056596 A1 * | 3/2007 | Fanney et al. | 128/898 |
| 2007/0179366 A1 * | 8/2007 | Pewzner et al. | 600/310 |
| 2007/0243521 A1 * | 10/2007 | Zuckerman | 435/4 |
| 2008/0021515 A1 * | 1/2008 | Horsager et al. | 607/54 |
| 2008/0068561 A1 * | 3/2008 | Kandel et al. | 351/221 |
| 2008/0254531 A1 * | 10/2008 | Zuckerman | 435/288.7 |
| 2008/0269629 A1 * | 10/2008 | Reiner | 600/544 |
| 2009/0221912 A1 | 9/2009 | Nelson et al. | |
| 2010/0103497 A1 * | 4/2010 | Rehn | 359/290 |

FOREIGN PATENT DOCUMENTS

| | | |
|---|---|---|
| JP | 04-017076 A | 1/1992 |
| WO | 9715229 | 5/1997 |
| WO | 9963882 A1 | 12/1999 |
| WO | 0006015 A1 | 2/2000 |
| WO | 0122741 A2 | 3/2001 |
| WO | 03083434 A2 | 10/2003 |
| WO | 2004004556 A1 | 1/2004 |
| WO | 2004049899 A2 | 6/2004 |
| WO | 2006121984 A2 | 11/2006 |

OTHER PUBLICATIONS

Holeman B et al., "Dynamic scene analysis for vessel structure determination", Southeastcon '89 proceedings, Energy and information technologies in southeast, Columbia, SC USA, Apr. 9, 1989, pp. 1072-1073.

Domingo J et al., "Irregular motion recovery in flourescein angiograms", Pattern Recognition Letters, North-Holland Publ. Amsterdam, vol. 18, No. 8, Aug. 1, 1997, pp. 805-821.

Sklenar J et al., "Parametric imaging for myocardial contrast echocardiography: pixel-by-pixel incorporation of information from both spatial and temporal domains", Computer in Cardiology 1998 Cleveland, OH, USA, Sep. 13-16, 1998, pp. 461-464.

R.A. Linsenmeier, et al., "Metabolic dependence of photoreceptors on the choroids in the normal and detached retina", Published in Investigative Ophthalmology and Visual Science, vol. 41(10), pp. 3117-3123, Sep. 2000.

R. A. Linsenmeier et al., "Retinal hypoxia in long-term diabetic cats", Published in Investigative Ophthalmology and Visual Science, vol. 39(9), pp. 1647-1657, Aug. 1998.

Kurt R. Denninghoff et al., "Retinal imaging techniques in diabetes", Published in Diabetes Technology & Therapeutics, vol. 2, No. 1 (2000), pp. 111-113.

M. Bruce Shields, "Textbook of Glaucoma", Published by Lippincott Williams and Wilkins (Philadelphia), 1997.

Wong T. Y. et al./, "White matter lesions, retinopathy, and incident clinical stroke", JAMA 288(1), pp. 67-74 (2002).

Wong T. Y et al., "Retinal arteriolar narrowing and risk coronary heart disease in men and women. The atherosclerosis risk in communities study", JAMA; 287(9), pp. 1153-1159, (2002).

H. H. Quick et al., "MR Imaging of the Vessel wall", Published in Eur. Radio, vol. 12(4), pp. 889-900, Apr. 2002.

Dormandy et al., "Lower-extremity arteiosclerosis as a reflection of a systemic process: implications for concomitant coronary and carotid disease", Published in Semin. Vasc. Surg. pp. 118-112, vol. 12(2), Jun. 1999.

Kutzner et al., "Fatal lipid embolism following intra-arterial angiography as an early stage of anteriosclerosis", Published in British Journal of Radiology, vol. 73,(874), pp. 1108-1111, Oct. 2000.

Wong T. Y. et al., "Retinal microvascular abnormalities and incident stroke: the atherosclerosis risk in communities study", Lancet, 358(9288), pp. 1134-1140 (2001).

"Finite element modeling of three-diimensional pulsatile flow in the abdominal aorta: Rellevance to atherosclerosis", Taylor et al., Annals of Biomedical Engineering, vol. 26, pp. 975-987 (1998).

"In vivo quantification of blood flow and wall shear stress in the human abdominal aorta during lower limb exercise", Taylor et al., Annals of Biomedical Engineering, vol. 30, pp. 402-408 (2002).

Michelson G. et al., "Flickering light increases retinal blood flow", Retina, 22(3): 336-343, Jun. 2002.

Grinvald A. et al., "In-vivo optical imaging of cortical architecture and dynamics", Published in Modern Techniques in Neuroscience Research, U. Windhorst and H. Johansson (eds.), Springer Verlag.

U. Seifert, W. Visler, "Retinal Vessel Analyzer (RVA)—Design and Function", Biomed Tech vol. 47, suppl. 1, (2002).

"Visual stimulus induced changes in human near-infrared fundus reflectance", by Abramoff, Invest Ophthalmol Vis Sci. Feb. 2006 47(2): 715-721.

Li J K-J, et al., "Noninvasive assessment of brain oxygenation and blood flow". Proceedings of the Annual Northeast Bioengineering Conference, 1990, vol. 16, 107-108.

\* cited by examiner

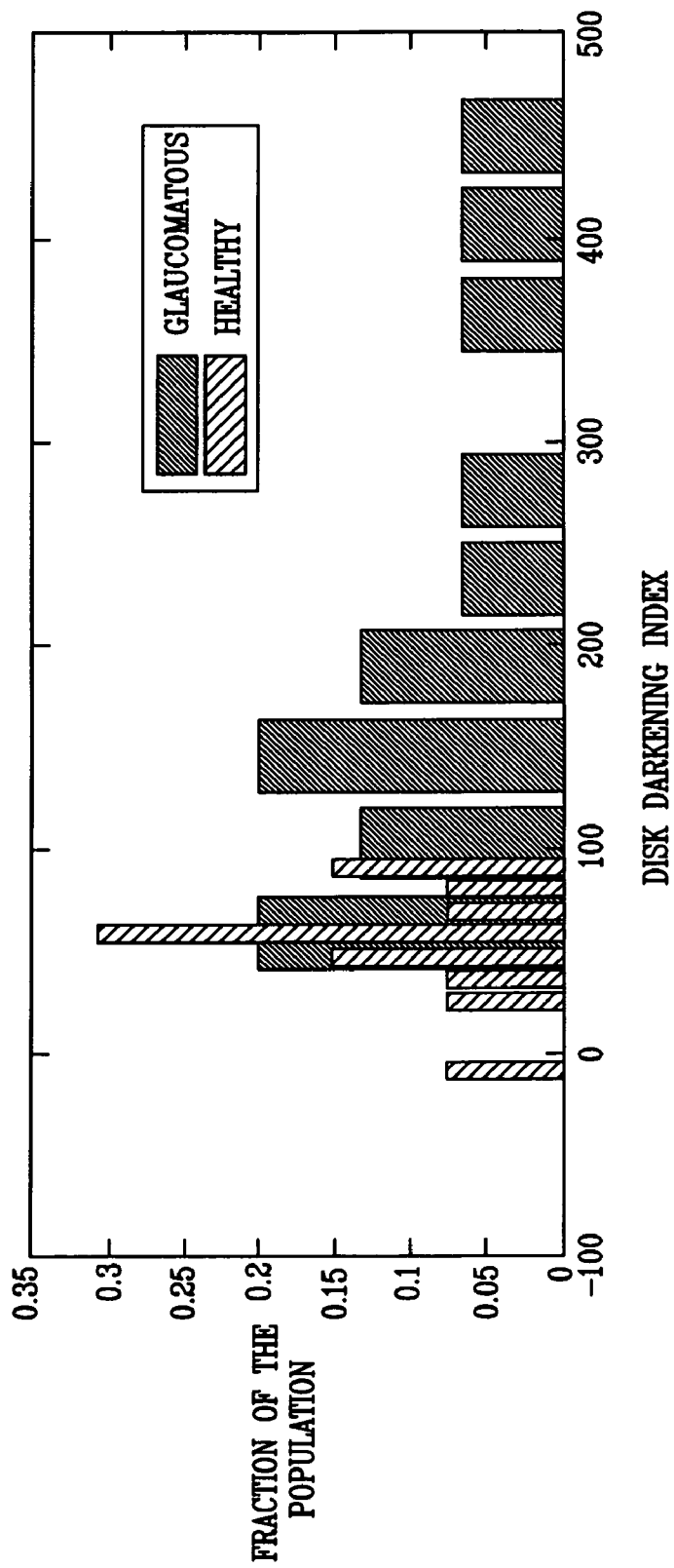

TIME-BASED IMAGING

CROSS-REFERENCES TO RELATED APPLICATIONS

The present application claims the benefit of U.S. Provisional Patent Application 61/009,055 to Grinvald et al., filed Dec. 20, 2007, which is incorporated herein by reference.

FIELD OF THE INVENTION

The present invention generally relates to external medical apparatus. Specifically, the present invention relates to retinal imaging.

BACKGROUND OF THE INVENTION

Diseases involving retinal vasculature are one of the leading causes of blindness worldwide. Many of these diseases are both progressive and treatable. Thus, their early detection is highly desirable. Diagnoses are often made on the basis of the many structural changes which may occur in the retina as a consequence of problems with retinal blood flow. These problems include neovascularization (the growth of new blood vessels in an attempt to compensate for a reduction in flow through pre-existing vessels), "cotton-wool" patches (regions in which nerve fiber axoplasmic transport has failed), the degeneration of cells of the eye, (e.g., retinal nerve fibers), and/or other metabolic or biochemical abnormalities. Once observed, these and other phenomena may be used to diagnose retinal vascular disease, and treatment may be initiated to inhibit further degeneration. It is desirable to detect such problems early, if possible, before irreversible damage has occurred.

US Patent Application Publication 2006/0147897 to Grinvald et al., which is incorporated herein by reference, describes a method and system for detecting abnormalities in the properties of the walls of a subject's blood vessels by observing the characteristics of blood flow in vessels which are optically accessible, such as the retinal vasculature. A time sequenced series of images is taken, and the images are processed to eliminate the background and render erythrocyte motion visible. Information about the state of the inner wall of the blood vessel which has been imaged is obtained from the characteristics of this blood flow. This information is described as being capable of being extrapolated to provide information about the state of the blood vessels elsewhere in the subject. In addition, a system and method are described for detecting arteriosclerotic plaque on the walls of blood vessels by labeling the plaque with a molecular label having desired optical or radioactive properties, and directly imaging the plaque either in an optically accessible blood vessel, or by imaging radioactive label in the plaque in a blood vessel anywhere in the body.

US Patent Application Publication 2006/0131284 to Grinvald et al., which is incorporated herein by reference, describes a method and system for determining and mapping the quantity of chromophores having a distinct spectrum attached to moving objects in a spectrally rich environment that may include multiple chromophores attached to stationary objects. An area of interest is imaged at different times and different wavelengths, and the spectral properties of the one or more chromophores attached to the moving objects are separated from the stationary spectral properties of the background, followed by spectral analysis of the moving objects to determine their quantity. Application to the retinal vasculature is illustrated, showing the imaging, analyzing and quantifying the oxygen saturation of retinal blood, resolved for the different vascular compartments: capillaries, arterioles, venules, arteries, and veins. Changes in the structure of the vascular environment are also determined (whether growth of new vessels or the elimination of existing ones), by the generation of path maps based on analysis of differential images taken at a single wavelength of the moving components in the blood flow.

U.S. Pat. No. 6,588,901 to Grinvald et al., which is incorporated herein by reference, describes a system for directly imaging and analyzing the movement of individual erythrocytes in blood vessels, the system comprising imaging means for acquiring, within a predetermined time interval from each other, at least one pair of images of at least one same erythrocyte for producing at least two frames, each image representing an analog or digital image of the location of the erythrocyte in each of the frames at a predetermined time; image acquisition means for collecting and storing analog or digital images in machine-readable form, and a computer for controlling the operation of the imaging means and the image acquisition means, for processing the at least two frames, and for analyzing the movement of the erythrocyte in the blood vessels. A method for directly imaging and analyzing the movement of individual erythrocytes in blood vessels is also provided.

U.S. Pat. No. 6,478,424 to Grinvald et al., which is incorporated herein by reference, describes a system for imaging reflectance changes, intrinsic or extrinsic fluorescence changes of a retina due to retinal function, including an imaging illuminator for illumination of the retina; a retina-stimulating illuminator for inducing a functional response; an imaging device receiving light from the retina via retinal imaging optics; image acquisition means for digitizing and storing images received from the imaging device, and a computer for controlling the operation of the system and for processing the stored images to reveal a differential functional signal corresponding to the retina's function.

The following patents and patent applications may be of interest:

PCT Publication WO 06/121,984 to Nelson et al.
U.S. Pat. No. 5,463,426 to Grinvald
PCT Publication Wo 04/049899 to Grinvald et al.
PCT Publication WO 03/083434 to Grinvald et al.
PCT Publication WO 99/063882 to Grinvald et al.
PCT Publication Wo 00/006015 to Grinvald et al.
U.S. Pat. No. 6,351,663 to Flower et al.
U.S. Pat. No. 5,279,298 to Flower
US Patent Application Publication 2002/0016533 to Marchitto et al.
U.S. Pat. No. 5,784,162 to Cabib et al.
U.S. Pat. No. 5,983,120 to Groner et al.
U.S. Pat. No. 6,902,935 to Kaufman
US Patent Application Publication 2002/0111545 to Lindberg
U.S. Pat. No. 6,104,939 to Groner The following articles may be of interest:

"Retinal microvascular abnormalities and incident stroke: the Atherosclerosis Risk in Communities Study," by Wong, Lancet 2001: 358:1134-40

"Automatic Extraction and Measurement of Leukocyte Motion in Microvessels Using Spatiotemporal Image Analysis," by Sato, IEEE Transactions on Biomedical Engineering, Vol. 44, No. 4, April 1997

"Visual stimulus induced changes in human near-infrared fundus reflectance," by Abramoff, Invest Opthalmol Vis Sci. 2006 February; 47(2): 715-721

SUMMARY OF THE INVENTION

In some embodiments of the present invention, a clinical state of a portion of a subject's body, for example, the subject's retina, is diagnosed in accordance with the following method:

(1) A first pulse of electromagnetic energy (e.g., a first flash of light) is directed toward the portion.

(2) While the portion is in a functional state due to the first pulse of electromagnetic energy, a second pulse of electromagnetic energy (e.g., a second flash of light) is directed toward the portion. At a "second-pulse" time (e.g., a "second-flash" time), light of the second pulse of electromagnetic energy that is reflected from the portion is detected.

(3) While the portion is in a functional state due to the first and second pulses of electromagnetic energy, a third pulse of electromagnetic energy (e.g., a third flash of light) is directed toward the portion. At a "third-pulse" time (e.g., a "third-flash" time), light of the third pulse of electromagnetic energy that is reflected from the portion is detected.

(4) In response to detecting the pulses of electromagnetic energy (e.g., the flashes of light) at the second-pulse time and the third-pulse time, a characteristic of the portion resulting from (a) the functional state due to the first pulse of electromagnetic energy and (b) the functional state due to the first and second pulses of electromagnetic energy is quantified. The clinical state of the subject is identified in response to quantifying the characteristic of the portion.

In some embodiments, second-flash and third-flash images are produced respectively from light detected at second-flash and third-flash times. For some applications, the relationship between a characteristic of the second image and a characteristic of the third image is quantified. Alternatively or additionally, a differential image is formed from the second-flash and the third-flash images, and a characteristic of the differential image is quantified. Typically, a region of interest (ROI) is identified in at least one of the images, and a characteristic of the ROI is quantified.

For some applications, at a "first-flash" time, light of the first flash of light that is reflected from the retina while the retina is in a state that is not a functional state due to a flash of light is detected. A characteristic of the retina is quantified, the characteristic resulting from (a) the functional state due to the first flash of light, (b) the functional state due to the first and second flashes of light, and (c) the state that is not an functional state due to a flash of light. In some embodiments, a first-flash image of the retina is obtained using the light of the first flash of light that is reflected from the retina. For some applications, a differential image is formed using the first-flash image and at least one of the second-flash and third-flash images.

In some embodiments of the invention, a portion of a subject's body is stimulated by one or more stimuli. A response of the portion of the body is detected by detecting, at first and second times, respective parameters of light that are reflected from the portion of the body. Respective images of the portion of the body are formed by processing respective parameters of light that are detected. A region of interest (ROI) of the portion of the body is identified based on data from at least one of the images. A measurable parameter of the ROI in response to at least one of the one or more stimuli is quantified. A clinical state of the subject is identified in response to the quantification.

In some embodiments, the one or more stimuli are applied to the subject's retina. Typically, the retina is stimulated with at least first and second flashes of light, the flashes of light being separated in time by between 300 ms and 10 sec, between 10 ms and 300 ms, or between 1 ms and 20 ms, for example, between 1 ms and 10 ms. In some embodiments, each of the flashes of light has a duration of less than 1 ms, or a duration of 0.1 ms to 10 ms. Alternatively, the first flash of light has a duration of less than 1 ms and the second flash of light has a duration of less than 4 ms. In some embodiments, the retina is stimulated with at least three flashes of light, the lengths of the flashes and the intervals between the flashes being as described hereinabove with respect to the first and second flashes. Light of respective flashes of light that is reflected from the retina is detected using a detector, for example, (a) a fundus camera, (b) an opthalmoscope, or (c) a CCD that is not part of a fundus camera. (Typically, a fundus camera includes a CCD, or another type of detector.) Images of the retina are formed by processing the detected light.

In some embodiments, the retina is stimulated by modulating the temperature of the retina, and/or by modulating the oxygen saturation of the retina. For example, the oxygen saturation of the retina may be modulated by providing, for inhalation by the subject, oxygen, or a mixture of oxygen and another gas, e.g., nitrogen. In such embodiments, in addition to the retina being stimulated, the retina is illuminated. Light of the illuminating light that is reflected from the retina is detected using a fundus camera, or a CCD that is not part of a fundus camera, to form images of the retina. Alternatively or additionally, ambient light that is reflected from the retina is detected to form images of the retina.

In some embodiments, the ROI is the subject's optic nerve head, which is commonly referred to (and which is referred to in this application) as the optic disk. In an embodiment, darkening (or brightening) of the images of the optic disc in response to the one or more stimuli is quantified. In some embodiments, darkening of the optic disk relative to its surroundings is quantified. The quantification of the darkening is used to identify clinical states of the subject's eye, brain, cardiovascular system, nervous system, or entire body. For some applications, darkening of images of the optic disk, or another ROI, is quantified to identify that the subject is suffering from glaucoma, age related macular degeneration, and/or diabetic retinopathy.

There is therefore provided, in accordance with an embodiment of the present invention, a method for diagnosing a clinical state of a portion of a body of a subject, including:

(1) directing toward the portion a first pulse of electromagnetic energy;

(2) while the portion is in a functional state due to the first pulse of electromagnetic energy, directing toward the portion a second pulse of electromagnetic energy;

(3) detecting, at a second-pulse time, energy of the second pulse of electromagnetic energy that is reflected from the portion;

(4) while the portion is in a functional state due to the first and second pulses of electromagnetic energy, directing toward the portion a third pulse of electromagnetic energy;

(5) detecting, at a third-pulse time, energy of the third pulse of electromagnetic energy that is reflected from the portion;

(6) in response to detecting the pulse of electromagnetic energy at the second-pulse time and the third-pulse time, quantifying a characteristic of the portion resulting from (a) the functional state due to the first pulse of electromagnetic energy and (b) the functional state due to the first and second pulses of electromagnetic energy; and (7) identifying a clinical state of the subject in response to quantifying the characteristic of the portion.

In an embodiment:

the first pulse of electromagnetic energy includes a first flash of light, and step (1) includes directing the first flash of light toward the portion;

the second pulse of electromagnetic energy includes a second flash of light, and step (2) includes, while the portion is in a functional state due to the first flash of light, directing the second flash of light toward the portion;

the second-pulse time includes a second-flash time, and step (3) includes detecting, at the second-flash time, light of the second flash of light that is reflected from the portion;

the third pulse of electromagnetic energy includes a third flash of light, and step (4) includes, while the portion is in a functional state due to the first and second flashes of light, directing toward the portion the third flash of light;

the third-pulse time includes a third-flash time, and step (5) includes detecting, at a third-flash time, light of the third flash of light that is reflected from the portion; and step (6) includes, in response to detecting the flashes of light at the second-flash time and the third-flash time, quantifying a characteristic of the portion resulting from (a) the functional state due to the first flash of light and (b) the functional state due to the first and second flashes of light.

In an embodiment, the portion of the body includes a retina of the subject and directing the first, second, and third flashes of light toward the portion of the body includes directing the first, second, and third flashes of light toward the subject's retina.

In an embodiment, identifying the clinical state of the subject includes identifying a clinical state of a part of a body of the subject selected from the group consisting of: a brain, a cardiovascular system, and a nervous system.

In an embodiment, detecting the light of the second and third flashes of light reflected from the retina includes detecting the light of the second and third flashes of light reflected from the retina using a detecting device selected from the group consisting of: a fundus camera, a CCD, and an opthalmoscope.

In an embodiment, the method further includes detecting, at a first-flash time, light of the first flash of light that is reflected from the retina while the retina is in a state that is not a functional state due to a flash of light, and quantifying the characteristic of the retina includes quantifying a characteristic of the retina resulting from (a) the functional state due to the first flash of light, (b) the functional state due to the first and second flashes of light, and (c) the state that is not a functional state due to a flash of light.

In an embodiment, directing the first, second, and third flashes of light toward the retina includes directing the first, second, and third flashes of light toward the retina, each of the flashes of light having a duration of less than 1 ms.

In an embodiment, directing the first, second, and third flashes of light toward the retina includes directing the first, second, and third flashes of light toward the retina, each of the flashes of light having a duration of 0.1 ms to 10 ms.

In an embodiment, directing the first, second, and third flashes of light toward the retina includes directing the first, second, and third flashes of light toward the retina, a time interval between directing the first and the second flashes being equal to a time interval between directing the second and third flashes.

In an embodiment, directing the first, second, and third flashes of light toward the retina includes directing the first, second, and third flashes of light toward the retina, a time interval between directing the first and the second flashes being between 10 ms and 300 ms.

In an embodiment, directing the first, second, and third flashes of light toward the retina includes directing the first, second, and third flashes of light toward the retina, a time interval between directing the first and the second flashes being between 300 ms and 10 s.

In an embodiment, directing the first, second, and third flashes of light toward the retina includes directing the first, second, and third flashes of light toward the retina, a time interval between directing the first and the second flashes being between 1 ms and 20 ms.

In an embodiment, directing the first, second, and third flashes of light toward the retina includes directing the first, second, and third flashes of light toward the retina, a time interval between directing the first and the second flashes being between 1 ms and 10 ms.

In an embodiment, directing the first, second, and third flashes of light toward the retina includes directing the first, second, and third flashes of light toward the retina, a time interval between directing the first and the second flashes being different from a time interval between directing the second and third flashes.

In an embodiment, the method further includes directing one or more additional flashes of light toward the retina between directing the second and third flashes of light toward the retina.

In an embodiment, identifying the clinical state of the subject includes identifying a clinical state of an eye of the subject.

In an embodiment, identifying the clinical state of the subject includes identifying glaucoma of a retina of the subject.

In an embodiment, identifying the clinical state of the subject includes identifying a clinical state of a retina of the subject selected from the group consisting of: age related macular degeneration, and diabetic retinopathy.

In an embodiment, step (3) includes obtaining a second-flash image of the retina based on the light of the second flash of light that is reflected from the retina, and step (5) includes obtaining a third-flash image of the retina based on the light of the third flash of light that is reflected from the retina.

In an embodiment,
step (6) includes:
processing the second-flash and third-flash images of the retina to obtain a first differential image of the retina;
identifying a region of interest (ROI) of the differential image; and
computing a value that is representative of a darkness of the ROI of the differential image.

In an embodiment, processing the second-flash and third-flash images of the retina to obtain a first differential image of the retina includes dividing the third-flash image by the second-flash image.

In an embodiment, processing the second-flash and third-flash images of the retina to obtain a first differential image of the retina includes subtracting the second-flash image from the third-flash image.

In an embodiment, the method further includes:
at a first-flash time, detecting light of the first flash of light that is reflected from the retina;
obtaining a first-flash image of the retina based on the light of the first flash of light that is reflected from the retina; and
obtaining a second differential image of the retina by processing the first-flash image of the retina and an image selected from the group consisting of: the second-flash and third-flash images of the retina.

In an embodiment, the method further includes:
identifying a region of interest (ROI) of the second differential image; and
computing a value that is representative of a darkness of the ROI of the second differential image.

In an embodiment,
step (6) includes:
(a) identifying an ROI in the second-flash image;
(b) identifying an outer region of interest (OROI) in the second-flash image;
(c) computing a value (i-in) that is representative of an intensity of the ROI of the second-flash image;
(d) computing a value (i-out) that is representative of an intensity of the OROI of the second-flash image;
(e) computing an extent to which i-in and i-out in the second-flash image are distinct;
(f) identifying an ROI in the third-flash image;
(g) identifying an outer region of interest (OROI) in the third-flash image;
(h) computing a value (i-in) that is representative of an intensity of the ROI of the third-flash image;
(i) computing a value (i-out) that is representative of an intensity of the OROI of the third-flash image;
(j) computing an extent to which i-in and i-out in the third-flash image are distinct; and
(k) quantifying a relationship between (I) the extent to which i-in and i-out in the second-flash image are distinct, and (II) the extent to which i-in and i-out in the third-flash image are distinct.

In an embodiment, step (e) includes computing a ratio relating i-in to i-out in the second-flash image, and step (j) includes computing a ratio relating i-in to i-out in the third-flash image.

In an embodiment, step (e) includes computing an arithmetic difference between i-in and i-out in the second-flash image, and step (j) includes computing an arithmetic difference between i-in and i-out in the third-flash image.

In an embodiment, step (c) includes computing a mean intensity of the ROI in the second-flash image, step (d) includes computing a mean intensity of the OROI in the second-flash image, step (h) includes computing a mean intensity of the ROI in the third-flash image, and step (i) includes computing a mean intensity of the OROI in the third-flash image.

In an embodiment, step (c) includes computing a median intensity of the ROI in the second-flash image, step (d) includes computing a median intensity of the OROI in the second-flash image, step (h) includes computing a median intensity of the ROI in the third-flash image, and step (i) includes computing a median intensity of the OROI in the third-flash image.

In an embodiment, identifying the ROI in the second-flash image includes identifying a portion of the image that corresponds to an optic disk of the subject, and identifying the ROI in the third-flash image includes identifying a portion of the image that corresponds to an optic disk of the subject.

In an embodiment, identifying the OROI in the second-flash image includes identifying a strip that surrounds the ROI of the second-flash image, the strip having an area that is within 50% of an area of the ROI of the second-flash image, and identifying the OROI in the third-flash image includes identifying a strip that surrounds the ROI of the third-flash image, the strip having an area that is within 50% of an area of the ROI of the third-flash image.

In an embodiment, identifying the OROI in the second-flash image includes identifying an outer ring that is separated from the ROI of the second-flash image by an inner ring, and identifying the OROI in the third-flash image includes identifying an outer ring that is separated from the ROI of the third-flash image by an inner ring.

In an embodiment,
step (6) includes:
(a) processing the second-flash and the third-flash images to obtain a differential image;
(b) identifying an ROI of an image selected from the group consisting of: the second-flash and the third-flash images;
(c) identifying an ROI of the differential image, the ROI of the differential image corresponding to the ROI of the selected image;
(d) computing a value (r-in) that is representative of a darkness of the ROI of the differential image;
(e) computing a value (r-out) that is representative of a darkness of an outer region of interest (OROI) surrounding the ROI of the differential image; and
(f) quantifying a relationship between r-in and r-out.

In an embodiment, quantifying the relationship between r-in and r-out includes computing a ratio relating r-in to r-out.

In an embodiment, quantifying the relationship between r-in and r-out includes computing an arithmetic difference between r-in and r-out.

In an embodiment, computing r-in includes computing a mean darkness of the ROI, and computing r-out includes computing a mean darkness of the OROI.

In an embodiment, computing r-in includes computing a median darkness of the ROI, and computing r-out includes computing a median darkness of the OROI.

In an embodiment, step (b) includes identifying a portion of the selected image that corresponds to an optic disk of the subject.

In an embodiment, identifying the OROI includes identifying a strip that surrounds the ROI, the strip having an area that is within 50% of an area of the ROI.

In an embodiment, identifying the OROI includes identifying an outer ring that is separated from the ROI by an inner ring.

In an embodiment, quantifying a relationship between r-in and r-out includes:
computing a ratio relating r-in to r-out; and
subtracting the ratio from 1 to produce a result.

In an embodiment, identifying the clinical state of the subject includes identifying that the subject's retina is glaucomatous in response to the relationship between r-in and r-out passing a threshold.

In an embodiment, the method further includes identifying a severity of the glaucoma of the retina in response to the relationship between r-in and r-out.

The present invention will be more fully understood from the following detailed description of embodiments thereof, taken together with the drawings, in which:

BRIEF DESCRIPTION OF THE DRAWINGS

FIG. 5 is a histogram illustrating a disk darkness index of healthy subjects and glaucomatous subjects, defined in accordance with an embodiment of the present invention.

DETAILED DESCRIPTION OF EMBODIMENTS

Figure 1:
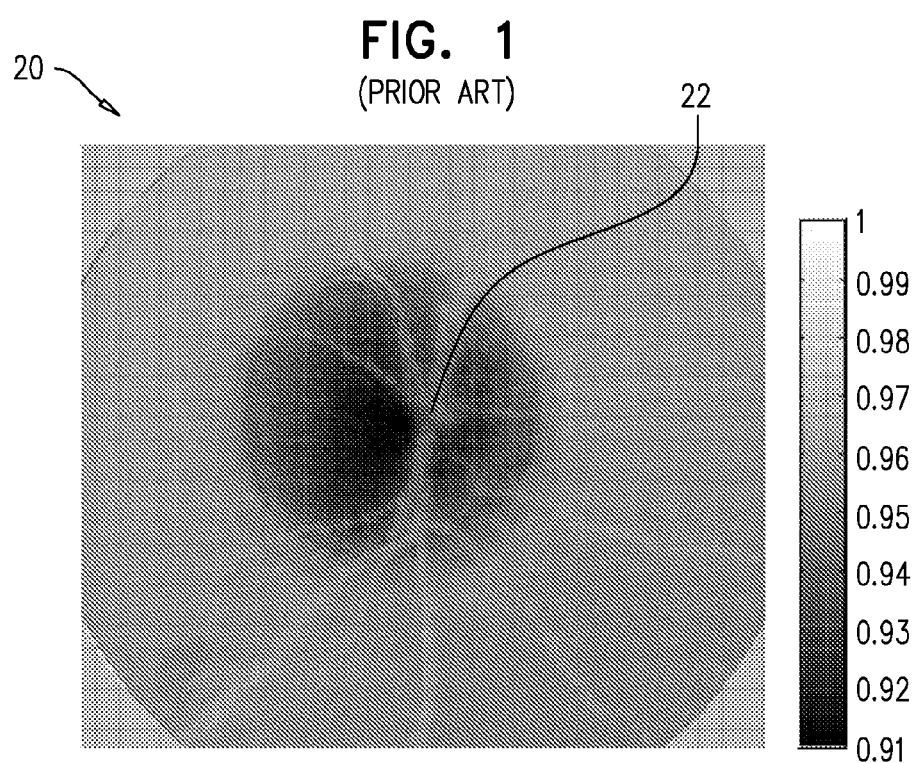
FIG. 1 is a differential retinal image, the image formed from raw retinal images, in accordance with an embodiment described in U.S. Pat. No. 6,478,424 to Grinvald et al.

Reference is now made to FIG. 1, which is a differential retinal image 20, the image formed from raw retinal images, in accordance with an embodiment described in U.S. Pat. No. 6,478,424 to Grinvald. Image 20 is a differential retinal image of a glaucomatous subject. Image 20 was formed by applying a first and a second flash of light to a subject's retina, the two flashes being separated by 17.5 ms. Light of the respective flashes that was reflected from the subject's retina was detected to form respective first and second images. The second image was divided by the first image to produce differential retinal image 20. It can be observed that there is a dark region 22 which is the region corresponding to the subject's optic disk. A color bar on the right side of FIG. 1 quantifies the level of darkness.

It is currently hypothesized by the inventors that the difference between the second image and the first image may be at least in part caused by the first flash of light, which was used to generate the first retinal image, also acting as a stimulus. The stimulus may cause a change to the functional state of the optic disk, which, in turn, causes a change in the appearance of the portion corresponding to the optic disk in the second retinal image. In the first retinal image, the eye was not stimulated, since the flash was too brief to evoke an activation before the first image was captured. Thus, the differential image may show the difference between the retina in activated and in inactivated states. Alternatively, differences between the first and second retinal images may have been for a different reason.

Figure 2:
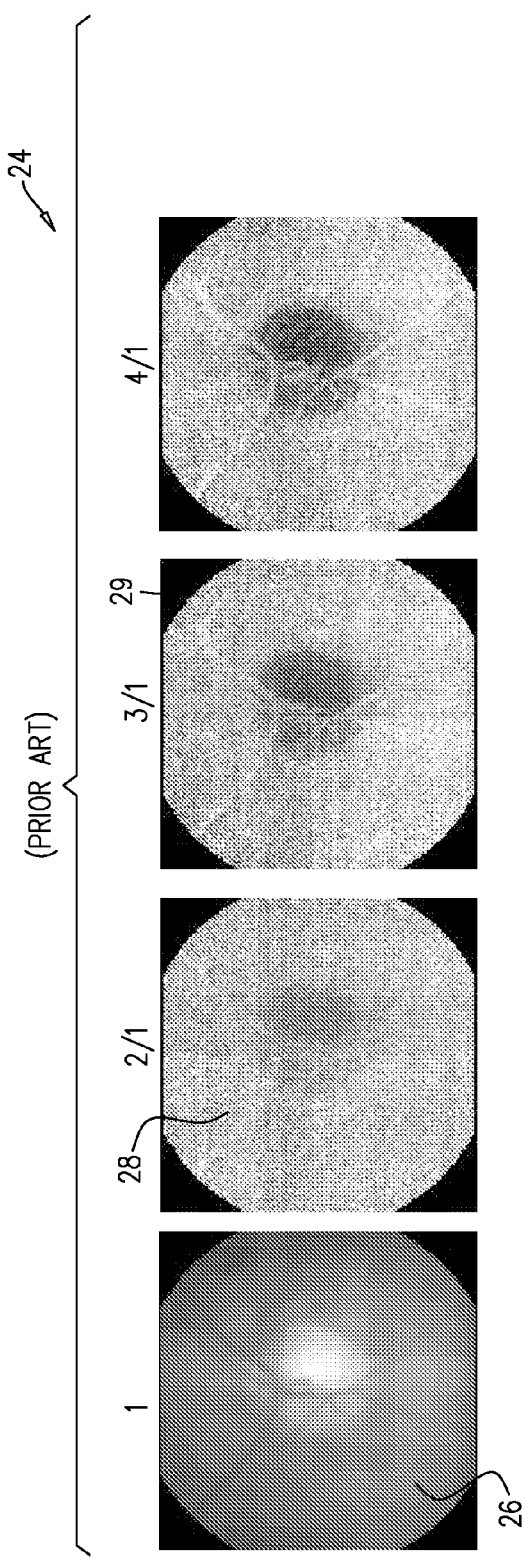
FIG. 2 is a series of differential retinal images, the images formed from raw retinal images, in accordance with an embodiment described in U.S. Pat. No. 6,478,424 to Grinvald et al.
Figure 2:
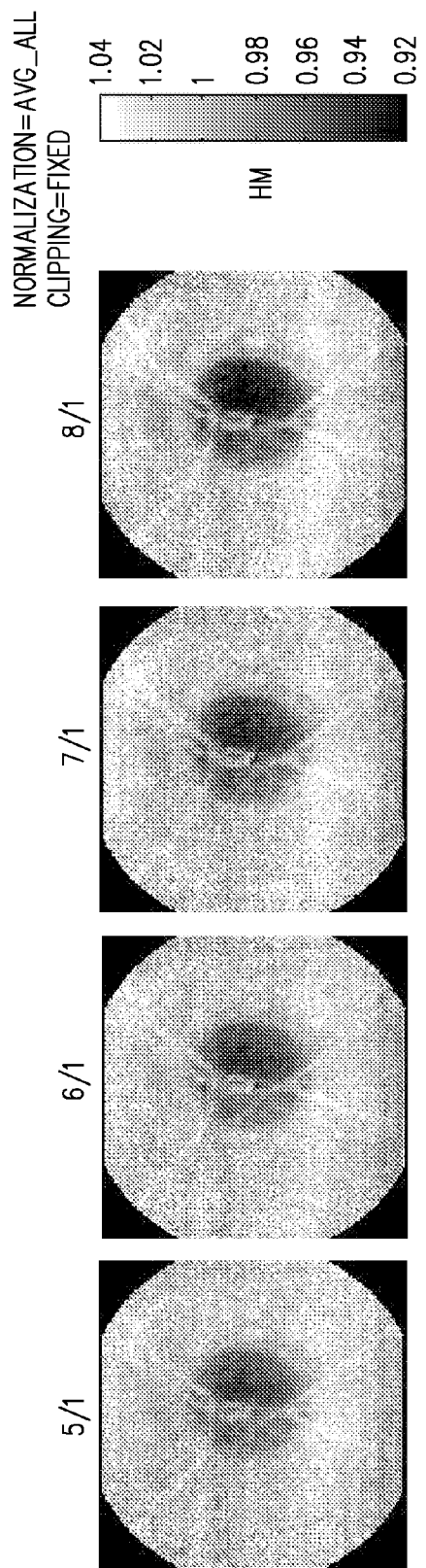

Reference is now made to FIG. 2, which is a series 24 of normalized retinal images, processed in accordance with an embodiment described in U.S. Pat. No. 6,478,424 to Grinvald. A glaucomatous subject's retina was stimulated by illuminating it with a sequence of eight flashes of light, the flashes of light being separated by 17.5 ms, in accordance with the methods described in the '424 patent. The light was passed through a 548 nm filter having a band width of 75 nm. Light of the respective stimuli that was reflected from the subject's retina was detected to form respective images.

A first image 26 of series 24 is a retinal image obtained from light of the first flash of light that was reflected by the retina. A second image 28 of series 24 is a differential retinal image that was formed by dividing a second retinal image by first image 26, the second retinal image having been obtained from light of the second flash of light that was reflected by the retina. A third image 29 of series 24 is a differential retinal image that was formed by dividing a third retinal image by first image 26, and so on. The inventors observed that there is a darkening of a portion of the differential retinal images. The darkened portion corresponds to the subject's optic disk.

It should be noted that although in series 24 there is a progressive darkening of the optic disk portion of the images, differential images may exhibit other effects. For example, there may be a lightening of the optic disc portion, the darkening may not progress in progressive differential images of a series, and/or there may be a change to a different portion of the images. In addition, other differential images could be formed and may exhibit similar effects. For example, a differential image may be formed by dividing a sixth retinal image in a series, by a third retinal image in the series, or by dividing a second retinal image in a series by a fourth retinal image in the series, and so on. Dividing a later image in the series by an earlier image in the series may show the difference between the retina (a) in an activated state due to having been stimulated m number of times and (b) in an activated state due to having been stimulated n number of times (where n≠m). For example, dividing the third image in the series by the second image may show the difference between the retina being in a functional state (a) due to the first and the second flashes of light and (b) due to the first flash of light.

Furthermore, differential images could be formed using retinal images that are separated from each other by intervals of time that are greater or less than 17.5 ms. In some embodiments, a second retinal image is separated in time from a first retinal image such that a functional change in the retina, caused by the flash used to generate the first image, is present, or maximized, when the second retinal image is generated.

In general, the specific parameters that are described with reference to the retinal images of FIGS. 1 and 2 are a description of how those specific images were generated. They do not limit the scope of the present invention.

Figure 3A:
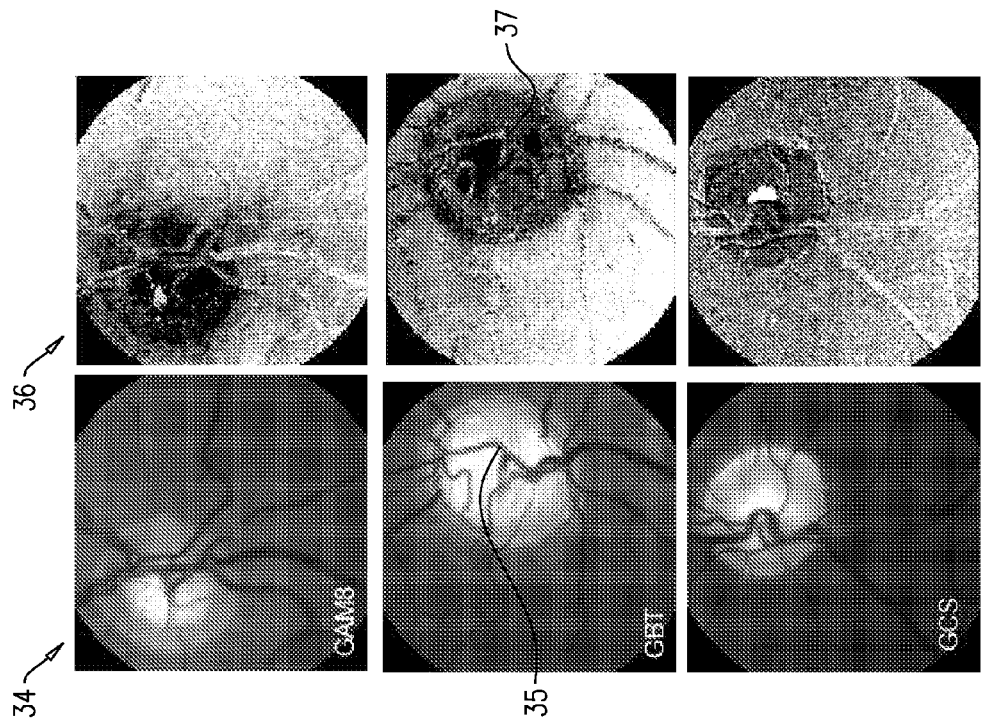
FIG. 3A is a set of retinal images and a corresponding set of differential retinal images of healthy subjects, formed in accordance with an embodiment of the present invention.
Figure 3B:
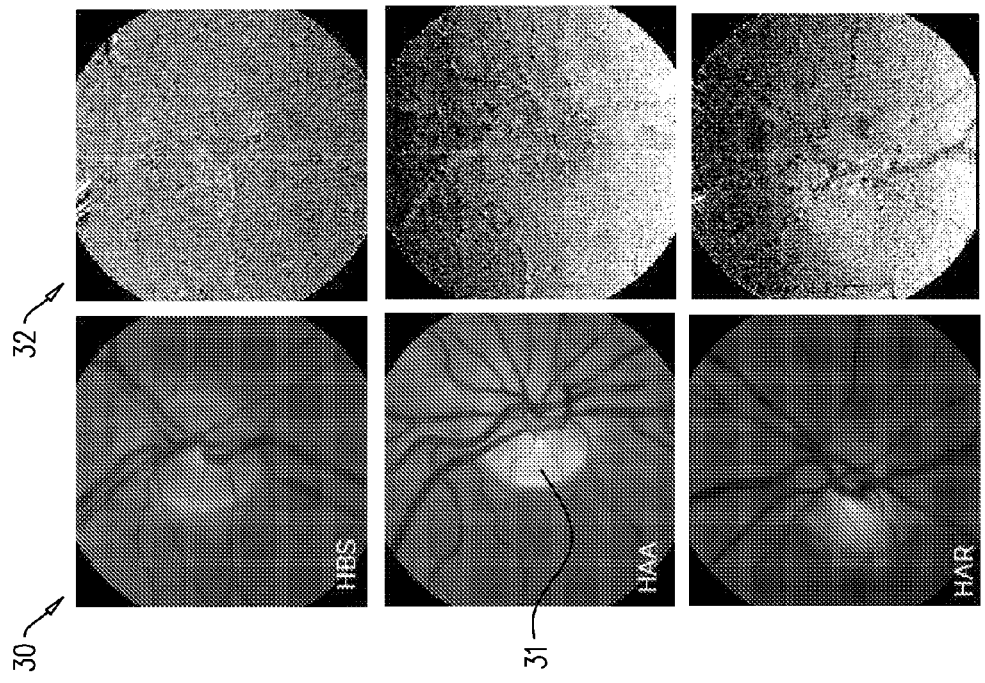
FIG. 3B is a set of retinal images and a corresponding set of differential retinal images of glaucomatous subjects, formed in accordance with an embodiment of the present invention.

Reference is now made to FIG. 3A, which is a set 30 of retinal images and a corresponding set 32 of differential retinal images of healthy subjects, formed in accordance with an embodiment of the present invention. The top retinal image of set 30 corresponds to the top differential retinal image of set 32, i.e., the two top images are a retinal image and a differential retinal image of the same eye. The middle image of set 30 corresponds to the middle image of set 32, and the bottom image of set 30 corresponds to the bottom image of set 32. The retinal images and differential retinal images of sets 30 and 32 are images of subjects who were known to have healthy retinas. It can be observed that in each of the retinal images of set 30, there is a bright portion (e.g., portion 31 of the middle image of set 30), which corresponds to the subject's optic disk. In the corresponding differential retinal images of set 32, the inventors observed that there is no consistent darkening of the portion corresponding to the optic disk. Reference is now made to FIG. 3B, which is a set 34 of retinal images and a corresponding set 36 of differential retinal images of glaucomatous subjects, processed in accordance with an embodiment of the present invention. The top retinal image of set 34 corresponds to the top differential retinal image of set 36, i.e., the two top images are a retinal image and a differential retinal image of the same eye. The middle image of set 34 corresponds to the middle image of set 36, and the bottom image of set 34 corresponds to the bottom image of set 36. The retinal images and differential retinal images of sets 34 and 36 are images of subjects who were known to have glaucomatous retinas. The inventors observed that in each of the retinal images of set 34, there is a bright portion (e.g., portion 35 of the middle image of set 34), which corresponds to the subject's optic disk. In the corresponding differential retinal images of set 36, there is darkening of the portion corresponding to the optic disk, for example, portion 37 of the middle image of set 36. The difference between the optic disk portion of the differential images of set 36, of the glaucomatous subjects, and the optic disk portion of the differential images of set 32, of the healthy subjects, indicated to the inventors that analyzing the optic disk portion of differential retinal images of a subject may provide an indication of whether the subject suffers from glaucoma.

Figure 4:
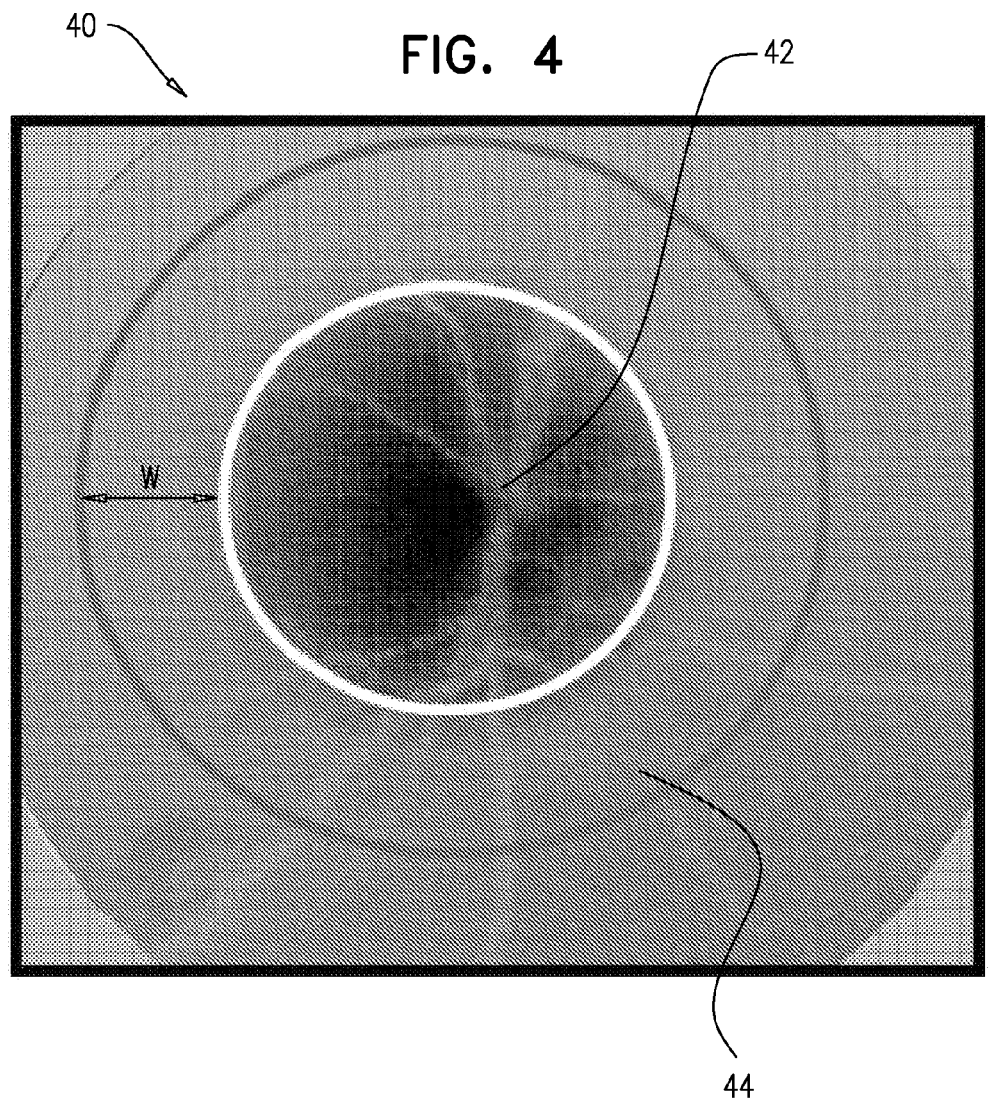
FIG. 4 is a differential retinal image showing a region of interest and an outer region of interest, defined in accordance with an embodiment of the present invention.

Reference is now made to FIG. 4, which is a differential retinal image 40 of a subject, showing a region of interest (ROI) 42 and an outer region of interest (OROI) 44, defined in accordance with an embodiment of the present invention.

In some embodiments of the invention, a subject's retina is stimulated by one or more stimuli, for example, by more than three stimuli. A response of the retina is detected by detecting light that is reflected from the retina. Respective images of the retina are obtained by detecting respective flashes of light that are reflected from the retina. For example, a first flash of light is directed toward the retina. While the retina is in a functional state due to the first flash, a second flash is directed toward the retina, and at a second-pulse time, light of the second flash that is reflected from the retina is detected. A second-flash image is obtained from the light detected at the second-flash time. While the portion is in a functional state due to the first and second flashes, a third flash is directed toward the retina and, at a third-pulse time, light of the third flash that is reflected from the portion is detected. A third-flash image is obtained from the light detected at the third-flash time.

In some embodiments, at a first-flash time, light of the first flash that is reflected from the retina is detected. For some applications, a first-flash image is obtained from the light detected at the first-flash time. In some embodiments, a differential image is formed by dividing one of the retinal images by a different retinal image, and/or by subtracting one of the retinal images from a different retinal image. For example, a differential image is formed by subtracting the second-flash image from the third-flash image, or by dividing the third-flash image by the second flash image. Alternatively or additionally, a differential image is formed by subtracting the first-flash image from the second-flash image, or by dividing the second-flash image by the first flash image In some embodiments, the time interval between the second and third flashes being directed toward the retina is equal to the time interval between the first and second flashes being directed toward the retina. Alternatively, the time intervals between the flashes are not equal. In some embodiments, the "second" flash and the "third" flash are not consecutive flashes. For example, one or more other flashes directed toward the retina may intervene between the second and third flashes.

ROI 42 of the retina is identified based on data from at least one of the images (i.e., one of the raw retinal images, and/or one of the differential retinal images). A measurable parameter of the ROI in response to at least one of the one or more stimuli is quantified. A clinical state of the subject is identified in response to the quantification.

Typically, ROI 42 is the portion of a retinal image corresponding to the subject's optic disk. In some embodiments, OROI 44 is a strip that surrounds, and is adjacent to, ROI 42. Alternatively, OROI 44 is a different shape, is not adjacent to the ROI, and/or is in a different portion of the retinal image. For example, the OROI may be a ring that is separated from the ROI by an inner ring. In some embodiments, the area of the OROI corresponds to the area of the ROI; for example, the OROI may have an area that is approximately equal to the area of the ROI. In an embodiment, the ratio of the area of the OROI to that of the ROI is between 4:4 and 6:4, e.g., 5:4. Typically, the area of the OROI is within 50% of the area of the ROI (i.e., $A(ROI)*0.5 < A(OROI) < A(ROI)*1.5$).

In some embodiments, ROI 42 is defined by analyzing a differential retinal image. Alternatively, ROI 42 is defined by defining, in a raw image of a subject's retina, an ROI that corresponds to the optic disk. The ROI of differential images of the subject's retina is defined by defining the region of the differential image that corresponds to the ROI of the raw image.

In some embodiments, a value that is representative of the darkness of ROI 42 of differential image 40 is computed, and a clinical state of the subject is identified in response to the computed darkness.

For some applications, an ROI and an OROI are defined in each of a first and a second raw retinal image, the first and the second images being separated in time. For example, the first and second raw retinal images may be the second and third images (and/or the first and second images) in a series of retinal images, acquired in accordance with techniques described herein. For each of the first and the second images, a value (i-in) that is representative of the intensity of the ROI of the image is computed. For example, i-in may be the mean intensity or the median intensity of the ROI. A second value (i-out) that is representative of the intensity of the OROI of the image is computed. For example, i-out may be the mean intensity or the median intensity of the OROI. The extent to which i-in and i-out in are distinct in each of the images is computed. For example, a ratio relating i-in to i-out, or an arithmetic difference between i-in and i-out, may be computed for each of the first and the second images. A relationship between the ratio relating i-in to i-out in the second image and the ratio relating i-in to i-out in the first image is quantified. Alternatively or additionally, a relationship between the arithmetic difference between i-in and i-out in the second image and the arithmetic difference between i-in and i-out in the first image is quantified. A clinical state of the subject is identified in response to the quantification.

In some embodiments, a value (r-in) that is representative of the darkness of ROI 42 of at least one differential image 40 is computed, the differential image having been formed in accordance with the techniques described herein. Similarly, a value (r-out) that is representative of the darkness of OROI 44 is computed. Typically, r-in and r-out are computed by finding the mean (or the median) intensity of ROI 42 and of OROI 44 respectively.

For some applications, a ratio relating r-in to r-out is calculated in order to provide an indication of the relative darkness of ROI 42 compared to OROI 44. Alternatively or additionally, an arithmetic difference between r-in and r-out is computed. Further alternatively or additionally, a disk darkness index (DDI) of the subject is calculated, in accordance with the following equation:

$$DDI = (1-c),$$

where $c = r\text{-}in/r\text{-}out$.

Reference is now made to FIG. 5, which is a histogram illustrating the disk darkness index of retinas (scaled up by a factor of 10,000) of healthy subjects and glaucomatous subjects, measured in accordance with an embodiment of the present invention. The subjects were tested by an ophthalmologist to determine whether their retinas were healthy or glaucomatous. The graph illustrates that the disk darkness index of healthy tested subjects was always below a threshold (100 in FIG. 5), whereas the disk darkness index of glaucomatous tested subjects was often greater than the threshold. The graph indicates that a subject may typically be identified as being glaucomatous by measuring the disk darkness index of the subject. In some embodiments of the invention, the disk darkness of a subject's retina may indicate the severity of glaucoma of the subject's retina.

In some embodiments, quantification of the darkening of an ROI of differential retinal images is used to identify clinical states of the subject's eye, brain, cardiovascular system, nervous system, or entire body. For example, for any given clinical state of interest (e.g., extent of atherosclerosis, epilepsy, multiple sclerosis, Parkinson disease), a healthy population DDI (or related index) is calculated based on a modest number of healthy subjects (e.g., 100 subjects), and a corresponding DDI is determined for patients diagnosed with the given clinical state. Individual patients suspected of or suffering from the given clinical state are compared to the DDI's for the two populations, to determine to which group they belong and/or to determine the extent of the pathology. For some applications, darkening of images of the optic disk is quantified to identify that the subject is suffering from glaucoma, age related macular degeneration, and/or diabetic retinopathy.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method for diagnosing a clinical state of a portion of a body of a subject, comprising:
    (1) causing the portion to enter a functional state, by directing toward the portion a first pulse of electromagnetic energy;
    (2) while the portion is in the functional state due to the first pulse of electromagnetic energy, directing toward the portion a second pulse of electromagnetic energy;
    (3) detecting with a detecting device, at a second-pulse time, energy of the second pulse of electromagnetic energy that is reflected from the portion;
    (4) while the portion is in a functional state due to the first and second pulses of electromagnetic energy, directing toward the portion a third pulse of electromagnetic energy;
    (5) detecting with the detecting device, at a third-pulse time, energy of the third pulse of electromagnetic energy that is reflected from the portion;
    (6) in response to detecting the energy of the second pulse of electromagnetic energy that is reflected from the portion at the second-pulse time and detecting the energy of the third pulse of electromagnetic energy that is reflected from the portion at the third-pulse time,
        quantifying a characteristic of the portion resulting from (a) the functional state due to the first pulse of electromagnetic energy and (b) the functional state due to the first and second pulses of electromagnetic energy; and
    (7) identifying a clinical state of the subject in response to quantifying the characteristic of the portion.

2. The method according to claim 1, wherein:
    the first pulse of electromagnetic energy includes a first flash of light, and step (1) comprises directing the first flash of light toward the portion;
    the second pulse of electromagnetic energy includes a second flash of light, and step (2) comprises, while the portion is in a functional state due to the first flash of light, directing the second flash of light toward the portion;
    the second-pulse time includes a second-flash time, and step (3) comprises detecting, at the second-flash time, light of the second flash of light that is reflected from the portion;
    the third pulse of electromagnetic energy includes a third flash of light, and step (4) comprises, while the portion is in a functional state due to the first and second flashes of light, directing toward the portion the third flash of light;
    the third-pulse time includes a third-flash time, and step (5) comprises detecting, at a third-flash time, light of the third flash of light that is reflected from the portion; and
    step (6) comprises,
        in response to detecting, at the second-flash time, light of the second flash of light that is reflected from the portion, and detecting, at the third-flash time, light of the third flash of light that is reflected from the portion,
        quantifying a characteristic of the portion resulting from (a) the functional state due to the first flash of light and (b) the functional state due to the first and second flashes of light.

3. The method according to claim 2, wherein the portion of the body includes a retina of the subject and wherein directing the first, second, and third flashes of light toward the portion of the body comprises directing the first, second, and third flashes of light toward the subject's retina.

4. The method according to claim 3, wherein identifying the clinical state of the subject comprises identifying a clinical state of a part of a body of the subject selected from the group consisting of: a brain, a cardiovascular system, and a nervous system.

5. The method according to claim 3, wherein detecting the light of the second and third flashes of light reflected from the retina comprises detecting the light of the second and third flashes of light reflected from the retina using a detecting device selected from the group consisting of: a fundus camera, a CCD, and an ophthalmoscope.

6. The method according to claim 3, further comprising detecting, at a first-flash time, light of the first flash of light that is reflected from the retina while the retina is in a state that is not a functional state due to a flash of light, and wherein quantifying the characteristic of the retina comprises quantifying a characteristic of the retina resulting from (a) the functional state due to the first flash of light, (b) the functional state due to the first and second flashes of light, and (c) the state that is not a functional state due to a flash of light.

7. The method according to claim 3, wherein directing the first, second, and third flashes of light toward the retina comprises directing the first, second, and third flashes of light toward the retina, each of the flashes of light having a duration of less than 1 ms.

8. The method according to claim 3, wherein directing the first, second, and third flashes of light toward the retina comprises directing the first, second, and third flashes of light toward the retina, each of the flashes of light having a duration of 0.1 ms to 10 ms.

9. The method according to claim 3, wherein directing the first, second, and third flashes of light toward the retina comprises directing the first, second, and third flashes of light toward the retina, a time interval between directing the first and the second flashes being equal to a time interval between directing the second and third flashes.

10. The method according to claim 9, wherein directing the first, second, and third flashes of light toward the retina comprises directing the first, second, and third flashes of light toward the retina, a time interval between directing the first and the second flashes being between 10 ms and 300 ms.

11. The method according to claim 9, wherein directing the first, second, and third flashes of light toward the retina comprises directing the first, second, and third flashes of light toward the retina, a time interval between directing the first and the second flashes being between 300 ms and 10 s.

12. The method according to claim 9, wherein directing the first, second, and third flashes of light toward the retina comprises directing the first, second, and third flashes of light toward the retina, a time interval between directing the first and the second flashes being between 1 ms and 20 ms.

13. The method according to claim 12, wherein directing the first, second, and third flashes of light toward the retina comprises directing the first, second, and third flashes of light toward the retina, a time interval between directing the first and the second flashes being between 1 ms and 10 ms.

14. The method according to claim 3, wherein directing the first, second, and third flashes of light toward the retina comprises directing the first, second, and third flashes of light toward the retina, a time interval between directing the first and the second flashes being different from a time interval between directing the second and third flashes.

15. The method according to claim 14, further comprising directing one or more additional flashes of light toward the retina between directing the second and third flashes of light toward the retina.

16. The method according to claim 3, wherein identifying the clinical state of the subject comprises identifying a clinical state of an eye of the subject.

17. The method according to claim 16, wherein identifying the clinical state of the subject comprises identifying glaucoma of a retina of the subject.

18. The method according to claim 16, wherein identifying the clinical state of the subject comprises identifying a clinical state of a retina of the subject selected from the group consisting of: age related macular degeneration, and diabetic retinopathy.

19. The method according to claim 3, wherein step (3) comprises obtaining a second-flash image of the retina based on the light of the second flash of light that is reflected from the retina, and wherein step (5) comprises obtaining a third-flash image of the retina based on the light of the third flash of light that is reflected from the retina.

20. The method according to claim 19,
wherein step (6) comprises:
processing the second-flash and third-flash images of the retina to obtain a first differential image of the retina;
identifying a region of interest (ROI) of the differential image; and
computing a value that is representative of a darkness of the ROI of the differential image.

21. The method according to claim 20, wherein processing the second-flash and third-flash images of the retina to obtain a first differential image of the retina comprises dividing the third-flash image by the second-flash image.

22. The method according to claim 20, wherein processing the second-flash and third-flash images of the retina to obtain a first differential image of the retina comprises subtracting the second-flash image from the third-flash image.

23. The method according to claim 20, further comprising:
at a first-flash time, detecting light of the first flash of light that is reflected from the retina;
obtaining a first-flash image of the retina based on the light of the first flash of light that is reflected from the retina; and
obtaining a second differential image of the retina by processing the first-flash image of the retina and an image selected from the group consisting of: the second-flash and third-flash images of the retina.

24. The method according to claim 23, further comprising:
identifying a region of interest (ROI) of the second differential image; and
computing a value that is representative of a darkness of the ROI of the second differential image.

25. The method according to claim 19,
wherein step (6) comprises:
(a) identifying an ROI in the second-flash image;
(b) identifying an outer region of interest (OROI) in the second-flash image;
(c) computing a value (i-in) that is representative of an intensity of the ROI of the second-flash image;
(d) computing a value (i-out) that is representative of an intensity of the OROI of the second-flash image;
(e) computing an extent to which i-in and i-out in the second-flash image are distinct;
(f) identifying an ROI in the third-flash image;
(g) identifying an outer region of interest (OROI) in the third-flash image;
(h) computing a value (i-in) that is representative of an intensity of the ROI of the third-flash image;
(i) computing a value (i-out) that is representative of an intensity of the OROI of the third-flash image;
(j) computing an extent to which i-in and i-out in the third-flash image are distinct; and
(k) quantifying a relationship between (I) the extent to which i-in and i-out in the second-flash image are distinct, and (II) the extent to which i-in and i-out in the third-flash image are distinct.

26. The method according to claim 25, wherein step (e) comprises computing a ratio relating i-in to i-out in the second-flash image, and wherein step (j) comprises computing a ratio relating i-in to i-out in the third-flash image.

27. The method according to claim 25, wherein step (e) comprises computing an arithmetic difference between i-in and i-out in the second-flash image, and wherein step (j) comprises computing an arithmetic difference between i-in and i-out in the third-flash image.

28. The method according to claim 25, wherein step (c) comprises computing a mean intensity of the ROI in the second-flash image, wherein step (d) comprises computing a mean intensity of the OROI in the second-flash image, wherein step (h) comprises computing a mean intensity of the ROI in the third-flash image, and wherein step (i) comprises computing a mean intensity of the OROI in the third-flash image.

29. The method according to claim 25, wherein step (c) comprises computing a median intensity of the ROI in the second-flash image, wherein step (d) comprises computing a median intensity of the OROI in the second-flash image, wherein step (h) comprises computing a median intensity of the ROI in the third-flash image, and wherein step (i) comprises computing a median intensity of the OROI in the third-flash image.

30. The method according to claim 25, wherein identifying the ROI in the second-flash image comprises identifying a portion of the image that corresponds to an optic disk of the subject, and wherein identifying the ROI in the third-flash image comprises identifying a portion of the image that corresponds to an optic disk of the subject.

31. The method according to claim 30, wherein identifying the OROI in the second-flash image comprises identifying a strip that surrounds the ROI of the second-flash image, the strip having an area that is within 50% of an area of the ROI of the second-flash image, and wherein identifying the OROI in the third-flash image comprises identifying a strip that surrounds the ROI of the third-flash image, the strip having an area that is within 50% of an area of the ROI of the third-flash image.

32. The method according to claim 30, wherein identifying the OROI in the second-flash image comprises identifying an outer ring that is separated from the ROI of the second-flash image by an inner ring, and wherein identifying the OROI in the third-flash image comprises identifying an outer ring that is separated from the ROI of the third-flash image by an inner ring.

33. The method according to claim 19,
wherein step (6) comprises:
(a) processing the second-flash and the third-flash images to obtain a differential image;
(b) identifying an ROI of an image selected from the group consisting of: the second-flash and the third-flash images;
(c) identifying an ROI of the differential image, the ROI of the differential image corresponding to the ROI of the selected image;
(d) computing a value (r-in) that is representative of a darkness of the ROI of the differential image;
(e) computing a value (r-out) that is representative of a darkness of an outer region of interest (OROI) surrounding the ROI of the differential image; and
(f) quantifying a relationship between r-in and r-out.

34. The method according to claim 33, wherein quantifying the relationship between r-in and r-out comprises computing a ratio relating r-in to r-out.

35. The method according to claim 33, wherein quantifying the relationship between r-in and r-out comprises computing an arithmetic difference between r-in and r-out.

36. The method according to claim 33, wherein computing r-in comprises computing a mean darkness of the ROI, and wherein computing r-out comprises computing a mean darkness of the OROI.

37. The method according to claim 33, wherein computing r-in comprises computing a median darkness of the ROI, and wherein computing r-out comprises computing a median darkness of the OROI.

38. The method according to claim 33, wherein step (b) comprises identifying a portion of the selected image that corresponds to an optic disk of the subject.

39. The method according to claim 38, wherein identifying the OROI comprises identifying a strip that surrounds the ROI, the strip having an area that is within 50% of an area of the ROI.

40. The method according to claim 38, wherein identifying the OROI comprises identifying an outer ring that is separated from the ROI by an inner ring.

41. The method according to claim 38, wherein quantifying a relationship between r-in and r-out comprises:
computing a ratio relating r-in to r-out; and
subtracting the ratio from 1 to produce a result.

42. The method according to claim 38, wherein identifying the clinical state of the subject comprises identifying that the subject's retina is glaucomatous in response to the relationship between r-in and r-out passing a threshold.

43. The method according to claim 42, further comprising identifying a severity of the glaucoma of the retina in response to the relationship between r-in and r-out.

* * * * *